United States Patent [19]

Cavazza

[11] 4,268,524
[45] May 19, 1981

[54] METHOD OF TREATING ABNORMAL LIPOPROTEIN RATIOS WITH ACYLCARNITINE

[76] Inventor: Claudio Cavazza, 35, Via Marocco, 00144 Rome, Italy

[21] Appl. No.: 165,351

[22] Filed: Jul. 2, 1980

Related U.S. Application Data

[63] Continuation-in-part of Ser. No. 8,392, Feb. 1, 1979.

[30] Foreign Application Priority Data

Feb. 3, 1978 [IT] Italy ................................ 47900 A/78
May 15, 1978 [IT] Italy ................................ 49354 A/78

[51] Int. Cl.$^3$ ........................ A61K 31/22; A61K 31/23
[52] U.S. Cl. .................................... 424/311; 424/312; 424/314
[58] Field of Search ................ 424/311, 312, 313, 314

[56] References Cited

U.S. PATENT DOCUMENTS

| | | | |
|---|---|---|---|
| 3,810,994 | 5/1974 | Wiegand | 424/316 |
| 3,968,241 | 7/1976 | Defelice | 424/319 |
| 4,032,641 | 6/1977 | Chibata | 424/266 |
| 4,075,352 | 2/1978 | Defelice | 424/319 |
| 4,194,006 | 3/1980 | Cavazza | 424/311 |

OTHER PUBLICATIONS

Challoner, J. Clin. Invst., vol. 51, Aug. 1972, pp. 2071-2076.
Fritz, Chem. Abs., vol. 59, 1963, p. 10403.
Fraenkel, Vitamins & Hormones, Acd. Press, N.Y., vol. XV, 1957, pp. 73-118.
Preziosi, Lipid Pharm., Med. Chem. Series, vol. 2, 1964, Acd. Press, N.Y., pp. 446-450.
Gemelli, Boll. Della Soc. Ital. di. Biol. Sperimen., vol. 50, No. 10, 1974, pp. 667-672.
Bekaert (1) Chem. Abs., vol. 54, 1960, p. 14447e.
Bekaert (2) Chem. Abs., vol. 52, 1958, p. 18851e.
Borniche, Chem. Abs., vol. 54, 1960, p. 14447e.
Branca, Chem. Abs., vol. 87, 1977, Ab. No. 100942y.

*Primary Examiner*—Anna P. Fagelson
*Attorney, Agent, or Firm*—Jacobs & Jacobs

[57] ABSTRACT

Abnormally high ratios of low density and very low density lipoproteins to high denisty lipoproteins, an etiological factor in vascular conditions, are reduced by oral or parenteral administration of acylcarnitine which increases the level of high density lipoproteins.

5 Claims, No Drawings

METHOD OF TREATING ABNORMAL LIPOPROTEIN RATIOS WITH ACYLCARNITINE

CROSS-REFERENCE

This is a continuation-in-part of Ser. No. 8,392 filed Feb. 1, 1979.

DETAILED DESCRIPTION

β-Hydroxy-γ-trimethylaminobutyric acid is a well known compound, also known as carnitine, which has been safely used for a number of years for different indications. For example, the compound is sold in Europe as an appetite stimulant, and it has been reported that the material has an effect on the growth rate of children; see e.g. Borniche et al., Clinic Chemica Acta, 5, 171–176, 1960 and Alexander et al., "Protides in the Biological Fluids", 6th Colloquium, Bruges, 1958, 306–310. Investigation of the drug as an antagonist of thyroid hormone in cases of hyperthyroidism has also been reported, Gilgore et al., Journal of New Drugs, 6, No. 6, 319–320 (1966) and DeFelice et al., loc. cit., 6, No. 6, 351–353 (1966). U.S. Pat. No. 3,830,931 describes improvements in myocardial contractility and systolic rhythm in congestive heart failure which can often be obtained through administration of carnitine. U.S. Pat. No. 3,968,241 describes its use in cardiac arrhythmia. U.S. Pat. No. 3,810,994 describes the use of the compound in the treatment of obesity. Gemelli et al., Boll. Soc. Ital. Bio. Sper. 1974, 50(10), 667–672, reported a decrease in plasma cholesterol and lipoprotein levels in healthy infants upon administration of carnitine, although Strack et al., "Protides of the Biological Fluids", 7th Colloquium, Bruges 1959, 263–267, found an increase in cholesterol levels upon administration while Frohlich et al., Metabolism 27 (5) 1978, 555–561 found no significant change in cholesterol or triglyceride levels upon administration to fasting mature and healthy humans.

Carnitine is normally present in the body where it exerts the function of a carrier of activated long-chain free fatty acids through the mitochondrial membrane. Since the mitochondrial membrane is impermeable to acyl CoA derivatives, long-chain free fatty acids can enter only when esterification with carnitine has tken place. The carrier function of carnitine is exerted both by transporting active long-chain fatty acids from the sites of their biosynthesis, for example the microsomes, to the mitochondria where they are oxidized, and by transporting acetyl CoA from the mitochondria, wherein it is formed, to the extramitochondrial sites where the synthesis of long-chain fatty acids occurs, e.g. in the microsomes wherein acetyl CoA can be utilized for synthesizing cholesterol and fatty acid.

The present invention is based on the discovery that acylcarnitines of the formula:

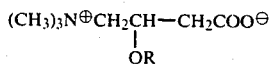

OR wherein R is acetyl, propionyl, butyryl, hydroxybutyryl, hexanoyl, octanoyl, decanoyl, palmitoyl, stearoyl, acetoacetyl, succinyl, isovaleryl, crotonyl, linoleyl, linolenyl or arachidonyl are of value in preventing or minimizing conditions which lead to infarction cardiac ischemia, cerebral ischemia and peripheral vascular disease. Preferably R is acetyl.

A high level of cholesterol and cholesterol precursors such as triglycerides in the plasma, generally characterized as hyperlipodemia, has long been associated with the etiology of vascular conditions such as infarctions, cardiac ischemia, cerebral ischemia and peripheral vascular diseases and various drugs such as nicotinic acid and its derivatives, triparanol, clofibrate and dexthrothyroxine have been used for the treatment of hyperlipodemia. It has been found, however, that they do not afford constantly reliable therapeutic results, they are generally toxic, particularly in long-term treatment, and exhibit untoward side effects. For instance, clofibrate has side effects including nausea, gastrointestinal discomfort, drowsiness, headache and dizziness. Weight gain, myalgia, pruritus, sk,in rashes, alopecia, and leucopenia also have been reported. Triparanol similarly demonstrates side effects to the extent it has been withdrawn from general clinical use.

In contrast to the findings of Gemelli et al, supra where the level of triglycerides and free fatty acids were not affected by carnitine per se, it has been found that a decrease in triglycerides and free fatty acids occurs upon the administration of acetylcarnitine. Moreover, and quite surprisingly, it has been found that the level of certain fractions of lipoproteins are actually increased upon administration of acetylcarnitine and that it is the relative level of these in the plasma, rather than the gross level of plasma cholesterol, which is therapeutically significant. In fact, a mere reduction in gross plasma cholesterol levels may be detrimental, as is discussed in greater detail hereafter.

Three distinct fractions of plasma lipoprotein can be detected electrophoretically [see Burstein et al., La presse Medicale 43 974 (1958)]. These are identified as high density lipoprotein, (HDL), low density lipoprotein (LDL) and very low density lipoprotein (VLDL). It now appears that while cholesterol is bound to lipoproteins of each fraction, conditions leading to vascular problems and which appeared grossly to be hypercholesterolemic are in fact an imbalance in the ratio of these fractions, specifically an abnormally high ratio of (LDL+VLDL)/HDL levels. Mere reduction in overall cholesterol levels does not mean this imbalance is corrected (and indeed it may be aggravated) since a reduction in HDL bound cholesterol without a greater decrease in LDL-bound and VLDL-bound cholesterol would increase the imbalance.

The present invention is based on the discovery that acylcarnitines will increase the level of high density lipoprotein so as to selectively reduce the ratio of low density and very low density lipoproteins to high density lipoproteins in patients in which that ratio is abnormally high. As has been noted, it is the abnormal ratio which leads to conditions such as infarction, cardiac ischemia, cerebral ischemia and peripheral vascular diseases, not the mere presence of high leveles of cholesterol.

This effect can be observed in recognized experimental models.

For example in the hypercholesterolemic diet fed rat (Nath et al., J. of Nutr. 1959, 67 289), administration of 200 mg/kg of L-acetylcarnitine or D,L-acetylcarnitine effected a reduction in serum total lipids and triglycerides. While this was matched by a significant reduction in both low density and very low density lipoproteins, the level of high density lipoproteins actually increased, which increase in HDL levels in turn decreased the (LDL+VLDL)/HDL ratio 1.61 to about 1.11. (A typical ratio in the same species fed a normal diet was 1.49). These data can be summarized as follows:

the ratio is abnormally high. Typically, a normal ratio is about 1.5 to 2.7.

This effect can be observed in various other species and upon other routes of administration, as shown in

TABLE 1

Effect of D,L-acetylcarnitine and L-acetylcarnitine on serum total lipid, triglyceride and lipoprotein level in the hypercholesterolemic diet fed rat.
Mean value ± SEM after seven days of diet and two treatments each day.

| Treatment | mg kg$^{-1}$ (oral) | diet | total lipids mg/100 ml | triglycerides mg/100 ml | Lipoproteins HDL % | VLDL % | LDL % | VLDL + LDL/HDL |
|---|---|---|---|---|---|---|---|---|
| Water | — | normal | 423.17 ± 31.42** | 112.61 ± 10.21** | 31.30 | 10.23 | 36.66 | 1.49 |
| Water | — | hyperchol. | 537.87 ± 32.18 | 200.27 ± 19.22 | 31.79 | 15.81 | 35.55 | 1.61 |
| D,L-acetyl-carnitine | 200 × 2 | hyperchol. | 418.25 ± 24.15** | 120.29 ± 25.57* | 38.45 | 12.15 | 29.96 | 1.09 |
| L-acetyl-carnitine | 200 × 2 | hyperchol. | 402.36 ± 21.17*** | 110.31 ± 10.36*** | 39.12 | 12.02 | 31.15 | 1.10 |

*P ≤ 5;
**P ≤ 1;
***P ≤ 0.1; (Student's "t" test), N = 9

The ability to reduce abnormally high

Table 2:

TABLE 2

Effect of D, L-acetylcarnitine on serum lipoprotein fraction in rabbit and dog:
Value two hours after i.p. treatment

| Animal | treatment | mg kg$^{-1}$ | HDL % | VLDL % | LDL % | VLDL + LDL/HDL |
|---|---|---|---|---|---|---|
| rabbit | saline | — | 19.63 | 40.02 | 40.99 | 4.12 |
|  | D,L-acetylcarnitine | 500 | 29.23 | 25.42 | 40.66 | 2.26 |
| dog | saline | — | 14.64 | 39.98 | 44.57 | 5.77 |
|  | D,L-acetylcarnitine | 250 | 34.45 | 19.31 | 33.42 | 1.53 |

N = 4 FOR RABBIT : 3 FOR DOG (LDL+VLDL)/HDL ratios may involve primarily the L-isomer and thus the ability of D,L-acylcarnitine racemate to increase the HDL level, thus decreasing the (LDL+VLDL)/HDL ratio, may be largely traceable to the presence of the L-isomer in the racemate.

It does not appear that acylcarnitine has any significant effect on triglyceride levels when these are at normal levels. The increase in HDL levels and the reduction of the (LDL+VLDL)/HDL ratio upon the administration of acylcarnitine occurs rather only when Administration of D,L-acylcarnitine at a multiple dose regimen of 500 mg t.i.d. to hyperlipodemic patients for 20 days effected a reduction in the (LDL+VLDL)/HDL ratio from 5.88 to 3.00, a decrease of 49%. This reduction was accompanied by reductions of 24.28% total lipids, 20% cholesterol and 14.1% triglycerides. These data are tabulated in Table #3.

TABLE 3

Effect of D,L-acetylcarnitine in hyperlipoproteinemic and hyperlipidaemic patients.

| | Total lipids mg/100 ml | Cholesterol mg/100 ml | Triglycerides mg/100 ml | HDL % | LDL % | VLDL % | VLDL + LDL/HDL |
|---|---|---|---|---|---|---|---|
| before treatment | 1380 | 290 | 256 | 16 | 57 | 37 | 5.88 |
| after treatment | 1045 | 232*** | 220** | 26** | 50* | 28** | 3.00 |
| variation % | −24.28 | −20 | −14.1 | +62 | −12.29 | −24.33 | |

*P < 5%
**P < 1%
***P < 0.1%
Student's "t"test (paired data)
N = 10

The effect of various acylcarnitines at different doses and with different routes of administration can be seen from Table 4:

TABLE 4

Effect of acylcarnitines on serum total lipids, triglycerides and cholesterol in the rat. Mean values ± SEM after treatment.

| treatment | mg kg$^{-1}$ | route | No. animals | min | Total lipids mg/100 ml | triglycerides mg/100 ml | cholesterol mg/100 ml |
|---|---|---|---|---|---|---|---|
| Water | — | oral | 5 | 60 | 3280.22 ± 15.95 | 113.06 ± 10.21 | 82.76 ± 2.58 |
| D,L-acetylcarnitine | 100 | oral | 5 | 60 | 295.14 ± 14.78*** | 96.54 ± 8.81 | 74.15 ± 2.03* |
| D,L-acetylcarnitine | 400 | oral | 5 | 180 | 267.36 ± 15.09*** | 87.38 ± 9.01 | 64.27 ± 3.26*** |
| L-acetylcarnitine | 100 | oral | 5 | 180 | 279.28 ± 13.87*** | 74.39 ± 8.15*** | 66.32 ± 2.75*** |
| D,L-proprionylcarnitine | 400 | oral | 5 | 60 | 320.45 ± 15.14** | 94.15 ± 9.34 | 75.48 ± 3.14 |
| D,L-hydroxybutyrylcarnitine | 400 | oral | 5 | 60 | 330.71 ± 13.92 | 92.18 ± 9.45 | 71.56 ± 2.64 |
| Saline | — | i.p. | 6 | 60 | 396.35 ± 16.41 | 106.85 ± 9.91 | 89.44 ± 3.31 |
| D,L-acetylcarnitine | 400 | i.p. | 6 | 60 | 252.14 ± 13.74*** | 74.78 ± 8.74*** | 66.38 ± 2.52*** |

TABLE 4-continued

Effect of acylcarnitines on serum total lipids, triglycerides and cholesterol in the rat. Mean values ± SEM after treatment.

| treatment | mg kg$^{-1}$ | route | No. animals | min | Total lipids mg/100 ml | triglycerides mg/100 ml | cholesterol mg/100 ml |
|---|---|---|---|---|---|---|---|
| L-acetylcarnitine | 100 | i.p. | 6 | 180 | 256.27 ± 14.06*** | 78.43 ± 6.15** | 67.46 ± 2.71*** |
| D-acetylcarnitine | 400 | i.p. | 6 | 60 | 310.78 ± 15.84*** | 94.18 ± 8.69 | 76.25 ± 3.44 |
| Saline | — | s.c. | 6 | 60 | 387.64 ± 15.88 | 112.33 ± 10.46 | 89.37 ± 3.44 |
| D,L-acetylcarnitine | 400 | s.c. | 6 | 60 | 299.37 ± 16.06*** | 74.18 ± 7.34*** | 68.35 ± 2.26*** |
| Saline | — | i.v. | 5 | 30 | 402.58 ± 16.25 | 109.46 ± 10.12 | 87.41 ± 2.26 |
| L-acetylcarnitine | 50 | i.v. | 5 | 30 | 335.46 ± 14.81*** | 88.15 ± 6.18* | 81.18 ± 2.35 |
| L-acetylcarnitine | 100 | i.v. | 5 | 30 | 284.18 ± 18.26*** | 72.26 ± 6.24*** | 71.26 ± 2.64*** |
| D-acetylcarnitine | 100 | i.v. | 5 | 30 | 351.86 ± 15.74 | 91.44 ± 8.36 | 78.45 ± 3.12 |
| D,L-propionylcarnitine | 100 | i.v. | 5 | 30 | 348.72 ± 14.36 | 86.37 ± 7.94 | 76.12 ± 3.47 |

*P ≤ 5%
**P ≤ 1%
***P ≤ 0.1%
Student's "t" test:

In actual practice, acylcarnitine is administered parenterally or orally in any of the usual pharmaceutical forms. These include solid and liquid oral unit dosage forms such as tablets, capsules, powders, solutions, syrups and the like, including sustained release preparations, and fluid injectable forms such as sterile solutions and suspensions. The term unit dosage form as used in this specifiction and the claims refer to physically discrete units to be administered in single or multiple dosage, each unit containing in association with the carrier, the predetermined quantity of acylcarnitine, or an equivalent amount of a pharmaceutically acceptable salt thereof, calculated to produce the desired effect upon administration of a specific number, one or more, of such units.

The dose which is administered should be determined having regard to the age, weight and condition of the patient, using sound professional judgment. Although effective results can be noticed at doses as low as from 5 to 8 mg/kg of body weight daily, a dose of from about 10 to about 50 mg/kg of body weight daily is preferred. Should it be deemed necessary, larger doses can be safely administered because of the extremely low toxicity of acylcarnitine. In view of the nature of the desired biochemical response, it is often desirable to divide the daily dosage into several administrations, utilizing a multidose regimen, the response being gauged in view of the total amount administered.

Typical examples of compositions for oral and parenteral administration are as follows:

EXAMPLE 1

Solution or sterile aqueous solutions in concentrations from 50 mg to 500 mg per ml.

A. An injectable composition (for ampoules/vials) is prepared as follows:

| | |
|---|---|
| L-acetylcarnitine | 50 mg |
| Sodium carboxymethyl cellulose (at low viscosity) | 10 mg |
| Polysorbate 80 | 4 mg |
| Propylparaben | 0.4 mg |
| Water for injections | q.s. 1 ml |

B. An intravenous composition is prepared in accordance with the following:

| | |
|---|---|
| L-acetylcarnitine | 1 g |
| NaCl | 8.6 g |
| KCl | 0.3 g |
| CaCl$_2$ | 0.33 g |
| Water for injections | q.s. 1 liter |

C. A composition for oral use is prepared in accordance with the following composition:

| | |
|---|---|
| D,L-acetylcarnitine | 5 g |
| Mannitol | 1.1 g |
| Sorbitol | 60 g |
| Sodium Benzoate | 300 mg |
| Orange Extract | 20 g |
| Vitamin B$_{12}$ | 300 mcg |
| Purified Water | q.s. 100 ml |

EXAMPLE 2

Tablets containing 20 mg of L-acetylcarnitine are prepared in accordance with the following:

| | |
|---|---|
| L-acetylcarnitine | 100 g |
| Starch | 450 g |
| Avicel | 450 g |
| Talc | 100 g |

The ingredients are thoroughly mixed and compressed into tablets of 0.1 g. weight.

EXAMPLE 3

Capsules containing from 500 mg of D, L-propionylcarnitine can be prepared without excipients or by admixture with an inert carrier and introduction into a gelatin sheath.

What is claimed is

1. The method of increasing the level of high density lipoproteins so as to selectively reduce the ratio of (a) low density and very low density lipoproteins to (b) high density lipoprotein in the plasma of a patient in which said ratio is abnormally high which comprises orally or parenterally administering to said patient in a single or multiple dose administration regimen an amount of an acylcarnitine of the formula

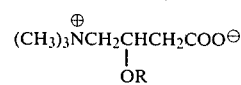

OR wherein R is acetyl, propionyl, butyryl, hydroxybutyryl, hexanoyl, octanoyl, decanoyl, palmitoyl, stearoyl, acetoacetyl, succinyl, isovaleryl, crotonyl, linoleyl, linolenyl or arachidonyl or a pharmaceutically acceptable salt thereof which is sufficient upon administration according to said regimen to reduce said abnormally high ratio.

2. The method according to claim 1 wherein said acylcarnitine is L-acetylcarnitine.

3. The method according to claim 1 wherein the total amount administered per day is from about 5 to about 50 mg of acylcarnitine, or an equivalent amount of a salt thereof, per kilogram of body weight.

4. The method according to claim 3 wherein the total amount administered per day is from about 10 to about 50 mg of acylcarnitine, or an equivalent amount of a salt thereof, per kilogram of body weight.

5. The method according to claim 1, wherein said acylcarnitine or said salt is administered orally.

* * * * *